(12) United States Patent
Kehler et al.

(10) Patent No.: US 8,592,449 B1
(45) Date of Patent: Nov. 26, 2013

(54) RADIOLABELLED PHENYLIMIDAZOLE-BASED LIGANDS

(75) Inventors: Jan Kehler, Lyngby (DK); Benny Bang-Andersen, Copenhagen S (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 13/890,705

(22) PCT Filed: Nov. 10, 2011

(86) PCT No.: PCT/DK2011/000132
§ 371 (c)(1),
(2), (4) Date: Aug. 1, 2013

(87) PCT Pub. No.: WO2012/062319
PCT Pub. Date: May 18, 2012

Related U.S. Application Data (60) Provisional application No. 61/411,934, filed on Nov. 10, 2010.

(30) Foreign Application Priority Data

Nov. 10, 2010 (DK) .................................. 2010 01023

(51) Int. Cl.
*A01N 43/42* (2006.01)
*A61K 31/44* (2006.01)

(52) U.S. Cl.
USPC .......................................... 514/303; 546/119

(58) Field of Classification Search
USPC .......................................... 546/119; 514/303
See application file for complete search history.

(56) References Cited

FOREIGN PATENT DOCUMENTS

| WO | 2009/152825 A1 | 12/2009 |
|---|---|---|
| WO | 2009152825 | * 12/2009 |
| WO | 2010/097367 A1 | 9/2010 |

* cited by examiner

*Primary Examiner* — Niloofar Rahmani
(74) *Attorney, Agent, or Firm* — Mary Catherine Di Nunzio (57) ABSTRACT

The present invention relates to radiolabelled PDE10A ligands which are useful for imaging and quantifying the PDE10A enzyme using positron emission tomography (PET).

17 Claims, 4 Drawing Sheets

RADIOLABELLED PHENYLIMIDAZOLE-BASED LIGANDS

CROSS-REFERENCE TO RELATED APPLICATIONS

The present application is a U.S. National Stage under 35 USC 371, which claims benefit of PCT/DK2011/000132 filed Nov. 10, 2011, which claims priority to Danish Application No. PA201001023 filed Nov. 10, 2010 and under 35 U.S.C. §119(e) of U.S. Provisional Application No. 61/411,934, filed Nov. 10, 2010.

FIELD OF THE INVENTION

The present invention relates to compounds suitable for labelling or already labelled with isotopes with short half lives such as $^{11}C$, $^{15}O$, or $^{18}F$, methods of preparing such compounds as well as use of such compounds as a PET ligand for determination of the binding occupancy of a PDE10A enzyme ligand at the PDE10A enzyme or for diagnostic imaging by positron emission tomography (PET).

BACKGROUND OF THE INVENTION

The PDE10A inhibitors can be used to raise levels of cAMP and/or cGMP within cells that express the PDE10A enzyme (or just PDE10A for short), especially neurons that comprise the basal ganglia, and PDE10A inhibitors would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of avoiding side effects, which are associated with the current therapies on the market.

WO 08/020,302 (Pfizer Products Incorporated) discloses the use of heteroaromatic quinolinebased compounds that serve as PDE10A inhibitors. WO09/152,825 (Lundbeck A/S) provides phenylimidazole derivative compounds that are PDE10A enzyme inhibitors, and as such are useful to treat neurodegenerative and psychiatric disorders.

A difficulty in the development of compounds useful for the treatment of neurological and psychiatric disorders has been the lack of appropriate animal models, the limited accessibility to the brain for pharmacokinetic measurements and lack of adequate direct biomarkers relating to action on the target system. Therefore, more accurate models for performing pharmacokinetic and pharmacodynamic modelling are desired and may be used along with e.g. plasma exposures. It is therefore clear that compounds that may lead to a better pharmacokinetic and pharmacodynamic modelling are valuable.

Non-invasive, nuclear imaging techniques can be used to obtain basic and diagnostic information about the physiology and biochemistry of living subjects. In nuclear imaging technique procedures, isotopes are combined with or chemically reacted with other chemical compounds or pharmaceuticals to form radiolabelled compounds. These compounds, once administered to the living subject, can localize to e.g. specific organs, cellular receptors or enzymes. This property of radiopharmaceuticals allows nuclear imaging techniques the ability to produce images which reveal the distribution and concentration of the radiolabelled compound as a function of time.

Positron Emission Tomography (PET) is of particular interest for drug development because of its high sensitivity and ability to provide quantitative and kinetic data. To conduct a PET scan, a short-lived radioactive isotope is injected into the living subject, usually into blood circulation. The radioactive isotope is chemically incorporated into a biologically active molecule, in the case of the present invention the radioactive isotope is incorporated into a PDE10A inhibitor. The radioactive isotope undergoes positron emission decay which eventually leads to the production of annihilation (gamma) photons which are detected when they reach the scintillator in the scanning device. The PET technique therefore depends on radioactive isotopes which undergo positron emission decay. These radioisotopes include carbon-11 (also symbolized 11C or $^{11}C$), nitrogen-13 (also symbolized 13N or $^{13}N$), oxygen-15 (also symbolized 15O or $^{15}O$), and fluorine-18 (also symbolized 18F or $^{18}F$).

WO 2006/053785 (Glaxo Group Limited), WO 2006/075226 (Pfizer Products Inc.), WO 2009/033584 (Bayer Schering Pharma AG), and WO 2010/097367 (Janssen Pharmaceutica NV) disclose various radiolabelled compounds for positron emission tomography.

Celen et al. NeuroImage 2010, 52, Supplement 1, P. S15, Celen et al. The Journal of Nuclear Medicine 2010; 51: 1584-1591, and Tu et al. Nuclear Medicine and Biology 2010; 37: 509-516 disclose $^{18}F$ and $^{11}C$ labelled compounds for PET imaging of PDE10A enzymes in the brain.

SUMMARY OF THE INVENTION

The invention provides radiolabelled compounds that bind to PDE10A enzymes and as such are useful in position emission tomography. Accordingly, the present invention relates to a method for determining binding occupancy at the PDE10A enzyme of a PDE10A enzyme ligand by use of a PET ligand of the present invention.

Accordingly, in one aspect the present invention relates to compounds of formula I:

and the use hereof as a PDE10A enzyme ligand in PET imaging, wherein
the isotopes are selected from the group consisting of $^{11}C$, $^{15}O$, and $^{18}F$;
the group of R1-R7 are selected as follows:
when R1 is a radiolabelled group incorporating or consisting of an isotope selected from $^{11}C$, $^{15}O$, and $^{18}F$, then R2-R7 is selected from H, F, methyl or methoxy; when one or more of R2-R7 is a radiolabelled group incorporating or consisting of an isotope selected from the group consisting of 11C, 15O, and 18F, then R1 is selected from H; C1-C6 alkyl such as methyl, ethyl, 1-propyl, 2-propyl, isobutyl; C1-C6 alkyl(C3-C8)cycloalkyl such as cyclopropylmethyl; C1-C6 hydroxyalkyl such as hydroxyethyl; fluoropropyl; fluoroethyl; and fluorobutyl.

In a further aspect the invention relates to salts or hydrates of the compounds of present invention.

In a still further aspect the invention relates to methods of production and use of the compounds of the present invention.

BRIEF DESCRIPTION OF DRAWINGS

The X-axis indicates time (minutes), the Y-axis indicates SUV

The X-axis indicates mg/kg of PF2545920, the Y-axis indicates % occupancy.

DETAILED DESCRIPTION OF THE INVENTION

The present invention relates to radiolabelled compounds, their production and the use of said compounds for PET imaging.

EMBODIMENTS ACCORDING TO THE INVENTION

In the following embodiments of the invention are disclosed. The first embodiment is denoted E1, the second embodiment is denoted E2 and so forth.

E1. A Compound according to Formula I

I comprising at least one isotope selected from the group consisting of C, $^{15}$O, and $^{18}$F, or a salt or a hydrate form of the compound.

E2. An embodiment according to Embodiment 1 where
R1 is a radiolabelled group comprising at least on isotope selected from the group consisting of $^{11}$C, $^{15}$O, and $^{18}$F, and
R2-R7 are individually selected from H, F, methyl or methoxy.

E3. An embodiment according to Embodiment 1 where
one or more of R2-R7 is a radiolabelled group comprising an isotope selected from the group consisting of $^{11}$C, $^{15}$O, and $^{18}$F, or one or more of R2-R5 is $^{18}$F, and
R1 is selected from H; C1-C6 alkyl, such as methyl, ethyl, 1-propyl, 2-propyl, isobutyl; C1-C6 alkyl(C3-C8)cycloalkyl, such as cyclopropylmethyl; C1-C6 hydroxyalkyl, such as hydroxyethyl; fluoropropyl; fluoroethyl; and fluorobutyl.

E4. The compound of E1 wherein R3, R4, and R5 are H and R7 is methyl.

E5. The compound of E2 and E4 wherein R2 is H and R6 is methyl.

E6. The compound according to E5 wherein R1 selected from the group consisting of $^{11}$CH$_3$, —CH$_2$$^{11}$CH$_3$, —$^{11}$CH$_2$CH$_3$, —CH$_2$CH$_2$$^{11}$CH$_3$CH, —$^{11}$CH$_2$CH$_2$CH$_3$, —$^{11}$CH$_2$CH$_2$CH$_2$CH$_3$, —CH$_2$CH$_2$CH$_2$$^{11}$CH$_3$, —CH$_2$CH$_2$$^{18}$F, —CH$_2$CH$_2$CH$_2$$^{18}$F, —CH$_2$CH$_2$CH$_2$CH$_2$$^{18}$F.

E7. The compound according to E3 and E4 wherein R1 and R6 are methyl.

E8. The compound according to E7 wherein R2 is O$^{11}$CH$_3$ ([$^{11}$C]methoxy).

E9. The compound according to E3 and E4 wherein R1 and R6 are methyl.

E10. The compound according to E9 wherein R2 is $^{18}$F.

E11. The compound according to E3 and E4 wherein R1 is CH$_3$ and R2 is H.

E12. The compound according to E11 wherein R6 is O$^{11}$CH$_3$ ([$^{11}$C]methoxy).

E13. The compound according to E1, wherein the compound is 5,8-Dimethyl-2-[2-([$^{11}$C-1-methyl]-4-phenyl-1H-imidazol-2-yl)-ethyl]-[1,2,4]triazolo[1,5-a]pyridine.

E14. The compound according to E1, wherein the compound is 8-[$^{11}$C]Methoxy-5-methyl-2-[2-(1-methyl-4-phenyl-1H-imidazol-2-yl)-ethyl]-[1,2,4]triazolo[1,5-a]pyridine).

E15. The compound according to E1, wherein the compound is 2-{2-[4-(2-[18F]Fluoro-phenyl)-1-methyl-1H-imidazol-2-yl]-ethyl}-5,8-dimethyl-[1,2,4]triazolo[1,5-a]pyridine.

E16. The compound according to E1, wherein the compound is 2-{2-[4-(2-[$^{11}$C]Methoxyphenyl)-1-methyl-1H-imidazol-2-yl]-ethyl}-5,8-dimethyl-[1,2,4]triazolo[1,5-a]pyridine.

E17. Use of a compound according to any of E1-E16 as a PET ligand.

E18. The use according to E17 for determination of the binding occupancy of a PDE10A enzyme ligand at the PDE10A enzyme.

E19. A method for the preparation of a compound according to any of E1-E16.

Substituents

The term "C1-C6 alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "C1-C6 hydroxyalkyl" refers to a C1-C6 alkyl group as defined above which is substituted with one hydroxy group.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methylpentoxy and n-hexyloxy.

The term "C3-C8 cycloalkyl" typically refers to cyclopropyl, cyclobutyl, cyclopentyl, cyclohexyl, cycloheptyl or cyclooctyl. The expression "C1-C6 alkyl(C3-C8)cycloalkyl" refers to a C3-C8 cycloalkyl as defined above which is substituted with a straight-chain or branched C1-C6 alkyl. Examples of such groups include, but are not limited to, cyclopropylmethyl.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, ptoluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Radiolabelled Compound

In the context of the present invention a radiolabelled compound is a compound comprising one or more isotopes selected from the group consisting of $^{11}C$, $^{15}O$, and $^{18}F$.

Radiolabelled Group

In the context of the present invention radiolabelled group is any of R1-R7 comprising at least one isotope selected from the group consisting of $^{11}C$, $^{15}O$, and $^{18}F$.

R1-R7 is short notation for the group consisting R1, R2, R3, R4, R5, R6, and R7.

Subsets of R1-R7 are defined similarly, e.g. R2-R6 means the group consisting R2, R3, R4, R5, and R6.

[11C]Lu AE92686

[11C]Lu AE92686 is the radiolabelled compound 5,8-dimethyl-2-[2-([$^{11}$C-1-methyl]-4-phenyl-1H-imidazol-2-yl)-ethyl]-[1,2,4]triazolo[1,5-a]pyridine

PF2545920

PF2545920 is the compound 2-[4-(1-methyl-4-pyridin-4-yl-1H-pyrazol-3-yl)-phenoxymethyl]-quinoline as disclosed in J. Med. Chem., 2009, 52 (16), pp 5188-5196.

Standardized Uptake Value (SUV)

Standardized uptake value, SUV, which is a PET quantifier, calculated as a ratio of tissue radioactivity concentration (e.g. in units kBq/ml) at time T, CPET(T) and injected dose (e.g. in units MBq) at the time of injection divided by body weight (e.g. in units kg).

EXAMPLES

Example 1

Preparation of the Compounds of the Invention

Scheme 1 represents a synthetic route towards compounds of formula I of the invention where R1 is a radiolabelled group. Unless otherwise indicated, in the reaction schemes and discussion that follow, R1-R7, are as defined above, Scheme 2 represents a synthetic route towards compounds of formula I of the invention where R6 is a radiolabelled group.

Scheme 3 represents a synthetic route towards compounds of formula I of the invention where R2 is a radiolabelled group.

Scheme 3

One example of a synthetic route for the synthesis of the PET-preursor compound of formula IIa is shown in scheme 4: The (5,8-Dimethyl-[1,2,4]triazolo[1,5-a]pyridin-2-ylmethyl)-triphenylphosphonium salt 1 is coupled under basic conditions with commercially available 4-phenyl-1H-imidazole-2-carbaldehyde 2 (Anichem Inc. catalog number FH10994) to form the 5,8-Dimethyl-2-[2-(4-phenyl-1H-imidazol-2-yl)-vinyl]-[1,2,4]triazolo[1,5-a]pyridine, compound 3.

The basic conditions are necessary in order to convert the phosphonium salt 1 into the corresponding Wittig-ylide compound 1A, which is the active nucleofile that condense with the aldehyde compound 2. Different bases can be used and DBU (1,8-Diazabicyclo[5.4.0]undec-7-ene) were found to give the best result. The product of the wittig reaction is the alkene compound 3, which is conveniently isolated in high yield and purity by precipitation from aqueous ethanol and can be used directly without further purification in the next step. The PET-preursor compound II is then formed from the alkene compound 3 by hydrogenation under a hydrogen atmosphere using a hydrogenation catalyst e.g. 5% palladium on charcoal.

Scheme 4

The syntheses of the starting material building block 1 is shortly described in the scheme 5, and the steps involved are:
1) To a solution of Ethyl O-mesitylsulfonylacetohydroxamate (43.50 g, 152.4 mmol) in 1,4-Dioxane (290 mL, 3700 mmol) cooled in an ice bath (freezes at 8-9° C.) was added 70% Perchloric acid (176.3 mL, 2.92 mol) dropwise over 15 minutes, maintaining internal temperature below 15° C. The mixture was then diluted with ice water (120 mL) to precipitate the product O-(mesitylsulfonyl)hydroxylamine which was filtered off, washed thoroughly with water, and immediately dissolved in (dichloromethane, DCM, 50 mL) while still wet. The organic layer was dried with $MgSO_4$ and filtered.

2) The obtained solution of O-(mesitylsulfonyl)hydroxylamine was added dropwise to a solution of commercially available 3,6-dimethyl-2-pyridinamine (16.4 g, 117 mmol) in DCM (100 mL) cooled in an ice bath. The mixture was then warmed to room temperature over 15 minutes. LCMS indicated almost complete conversion to the aminated intermediate.

3) The solvent was evaporated and the residue was dissolved in Methanol (600 mL, 10000 mmol) followed by the addition of 1,8-Diazabicyclo[5.4.0]undec-7-ene (31.438 mL, 210.22 mmol). The solution was stirred at RT for 5 minutes where Chloroacetic acid methyl ester (10.3 mL, 117 mmol) was added and the solution stirred at room temperature, RT, for 48 hours. The volatiles were removed in vacuo. Water was added and the organics extracted with EtOAc. The combined organics were washed with water, brine, dried ($MgSO_4$) filtered and the volatiles removed in vacuo. The residue was crystallised from heptane (400 mL), filtered and dried to yield 2-Chloromethyl-5,8-dimethyl-[1,2,4]triazolo[11,5-a]pyridine (7.414 g; Yield=31.5%; Purity=97%).

The syntheses of the PET-preursor compounds of formula II-V is performed by methods analogues to those described in scheme 5. The starting materials and other reagents are available commercially or can be synthesized by well-known and conventional methods for example as described in WO 2009/152825.

Example 2

Synthesis of [$^{11}$C]Lu AE92686: 5,8-Dimethyl-2-[2-([$^{11}$C-1-methyl]-4-phenyl-1H-imidazol-2-yl)-ethyl]-[1,2,4]triazolo[1,5-a]pyridine Production of [$^{11}$C]$CO_2$ and [$^{11}$C]methyl iodide A Scanditronix MC17 cyclotron was used to produce $^{11}$C via the $^{14}$N(p,alpha)$^{11}$C nuclear reaction. The target was filled with a mixture of 0.05% oxygen in nitrogen and bombarded with 17 MeV protons to produce [$^{11}$C]$CO_2$. The labeled carbon dioxide was reduced with 0.2 M lithium aluminium hydride in tetrahydrofuran. Treatment with 56% aqueous hydroiodic acid gave [$^{11}$C]methyl iodide which after drying with phosphorus pentoxide was used for the labeling of the precursor.

Synthesis of [$^{11}$C]Lu AE92686

The precursor (2.5 mg) was dissolved in 300 microL of dry dimethylformamide and approximately 2 mg of crushed sodium hydroxide was added. After thorough shaking, the clear liquid was transferred to another vial. The labeled methyl iodide was introduced and the reaction mixture was heated at 70° C. for 90 seconds. Water (450 microL) was then added and the diluted reaction mixture was injected onto the preparative HPLC column. The collection vial for the product fraction contained 5 mg of ascorbic acid.

Scheme 5

Isolation and Formulation

The solvent of the product fraction collected from the preparative chromatography was removed by means of a rotary evaporator and the residue was redissolved in 5 mL of sterile sodium chloride solution. When required for the biology experiments, the formulated tracer was filtered through a 0.2 micro m sterile filter.

The product was identified by analytical HPLC using co-injection of the non-radioactive reference compound by comparing the retention times of the UV and radioactive peaks. The total production time including formulation was about 30 minutes. A more rigorous identification of the tracer was done by LC/MS.

Example 3

Pharmacological Testing

PDE10A enzyme

Active PDE10A enzyme is prepared in a number of ways for use in PDE assays (Loughney, K. et al. Gene 1999, 234, 109-117; Fujishige, K. et al. Eur J. Biochem. 1999, 266, 1118-1127 and Soderling, S. et al. Proc. Natl. Acad. Sci. 1999, 96, 7071-7076). PDE10A can be expressed as full-length proteins or as truncated proteins, as long as they express the catalytic domain. PDE100A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and XhoI sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HClpH8.0, 1 mM $MgCl_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A PDE10A inhibition assay may for example, be performed as follows: The assay is performed in 60 microL samples containing a fixed amount of the relevant PDE enzyme (sufficient to convert 20-25% of the cyclic nucleotide substrate), a buffer (50 mM HEPES7.6; mM $MgCl_2$; 0.02% Tween20), 0.1 mg/mL BSA, 225 pCi of 3H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hour at room temperature before being terminated through mixing with 15 uL 8 mg/mL yttrium silicate SPA beads (Amersham). The beads are allowed to settle for one hour in the dark before the plates are counted in a Wallac 1450 Microbeta counter. The measured signal can be converted to activity relative to an uninhibited control (100%) and IC50 values can be calculated using the Xlfit extension to EXCEL.

In the context of the present invention the assay was performed in 60 micro L assay buffer (50 mM HEPES pH 7.6; 10 mM $MgCl_2$; 0.02% Tween20) containing enough PDE100A to convert 20-25% of 10 nM $^3$H-cAMP and varying amounts of inhibitors. Following one hour incubation the reactions were terminated by addition of 15 microL 8 mg/mL yttrium silicate SPA beads (Amersham). The beads were allowed to settle for one hour in the dark before the plates were counted in a Wallac 1450 Microbeta counter. IC50 values were calculated by non linear regression using XLfit (IDBS).

Results of the PDE10A inhibition assay showed that Lu AE92686 has a very high affinity for the PDE10A enzyme an IC50 value of 0.46 nM. Furthermore, Lu AE92686 is selective for the PDE10A enzyme over other receptors and enzymes screened to date (table 1).

TABLE 1

| Assay | Inhibition @ 10 μM (%) |
|---|---|
| A1 (h) (antagonist radioligand) | 2 |
| A1 (h) (agonist radioligand) | 4 |
| A2A (h) (agonist radioligand) | 24 |
| A3 (h) (agonist radioligand) | 32 |
| alpha 1A (h) (antagonist radioligand) | 33 |
| alpha 1B (h) (antagonist radioligand) | 26 |
| alpha 1D (h) (antagonist radioligand) | 16 |
| alpha 2A (h) (antagonist radioligand) | 13 |
| alpha 2B (h) (antagonist radioligand) | 33 |
| beta 1 (h) (agonist radioligand) | −4 |
| beta 2 (h) (agonist radioligand) | −6 |
| BZD (central) (agonist radioligand) | 3 |
| CB1 (h) (agonist radioligand) | 0 |
| CCK2 (CCKB) (h) (agonist radioligand) | 23 |
| D1 (h) (antagonist radioligand) | −3 |
| D2S (h) (antagonist radioligand) | 7 |
| D2S (h) (agonist radioligand) | 18 |
| D3 (h) (antagonist radioligand) | 4 |
| D4.4 (h) (antagonist radioligand) | 47 |
| ETA (h) (agonist radioligand) | −3 |
| GABAA (agonist radioligand) | −18 |
| H1 (h) (antagonist radioligand) | −5 |
| H2 (h) (antagonist radioligand) | 24 |
| H3 (h) (agonist radioligand) | 1 |
| MC4 (h) (agonist radioligand) | 3 |
| MT1 (ML1A) (h) (agonist radioligand) | 45 |
| MT3 (ML2) (agonist radioligand) | 94 |
| MAO-A (antagonist radioligand) | 2 |
| M1 (h) (antagonist radioligand) | −4 |
| M2 (h) (antagonist radioligand) | 20 |
| M3 (h) (antagonist radioligand) | 4 |
| M4 (h) (antagonist radioligand) | 18 |
| M5 (h) (antagonist radioligand) | 17 |
| NK1 (h) (agonist radioligand) | 29 |
| NK2 (h) (agonist radioligand) | 31 |
| Y1 (h) (agonist radioligand) | 9 |
| N neuronal alpha -BGTX-Insensitive (alpha 4beta 2) (agonist radioligand) | 12 |
| N muscle-type (h) (antagonist radioligand) | 0 |
| delta 2 (DOP) (h) (agonist radioligand) | 25 |
| kappa (KOP) (agonist radioligand) | 62 |
| mu (MOP) (h) (agonist radioligand) | 41 |
| PCP (antagonist radioligand) | −2 |
| rolipram (antagonist radioligand) | 31 |
| 5-HT1A (h) (agonist radioligand) | 89 |
| 5-HT1B (antagonist radioligand) | 18 |
| 5-HT2A (h) (antagonist radioligand) | 3 |
| 5-HT2B (h) (agonist radioligand) | 23 |
| 5-HT2C (h) (agonist radioligand) | 32 |
| 5-HT3 (h) (antagonist radioligand) | 1 |
| 5-HT4e (h) (antagonist radioligand) | 24 |
| 5-HT7 (h) (agonist radioligand) | 15 |
| sigma (non-selective) (agonist radioligand) | 8 |
| GR (h) (agonist radioligand) | 0 |
| UT (h) (agonist radioligand) | 9 |
| Ca2+ channel (L, dihydropyridine site) (antagonist radioligand) | 15 |
| Ca2+ channel (L, diltiazem site) (benzothiazepines) (antagonist radioligand) | 25 |
| Ca2+ channel (L, verapamil site) (phenylalkylamine) (antagonist radioligand) | 4 |

TABLE 1-continued

| Assay | Inhibition @ 10 µM (%) |
|---|---|
| Ca+ channel (N) (antagonist radioligand) | −8 |
| Na+ channel (site 2) (antagonist radioligand) | 36 |
| norepinephrine transporter (h) (antagonist radioligand) | 4 |
| dopamine transporter (h) (antagonist radioligand) | 7 |
| GABA transporter (antagonist radioligand) | −13 |
| choline transporter (CHT1) (h) (antagonist radioligand) | 12 |
| 5-HT transporter (h) (antagonist radioligand) | 6 |

Example 4

PDE10A Enzyme Localization in the Brain

Preparation

The monkey is sedated with ketamin (approximately 10 mg/kg), weighed, and maintained on a constant infusion of ketamin 15 mg/kg/h during transport. During transport the monkey is monitored by pulse oximetry and supported by oxygen. One venous catheter is applied for tracer administration and one venous catheter for blood radioactivity and PK sampling. Propofol is administered until the animal is anesthetized enough to intubate. After intubation the animal is maintained on sevoflurane inhalation anesthesia and artificial ventilation.

Blood Sampling

A 115 microL venous sample is taken at the induction of anesthesia and at the middle and end of experiment for estimation of electrolytes, glucose, hematocrite and glucose.

Blood samples (0.2 mL for radioactivity determination are taken at 0.5, 1, 3, 5, 10, 15, 20, 30, 45, 60 and 90 minutes after injection. The samples are labeled with time, date, sampling time in relation to injection, and project number.

Blood samples (2 mL) for metabolite analysis are obtained at 5, 30, and 90 minutes after injection of the tracer.

Blood sample (1.3 mL) for assessment of free tracer fraction in plasma is taken shortly before each tracer injection.

For PK analysis of the study drug, 0.5 mL blood samples are collected 1 minute after the end of each infusion and at 0.5, 15, 30, 60 and 90 minutes after injection of the radiolabelled compound. The samples are collected in tubes containing KaEDTA (Microvette 500 K3E, Sarstedt), which are inversed several times to ensure mixing of anticoagulant and blood and stored on ice. The blood samples are centrifuged within 30 minutes and plasma is transferred to a clean polypropylene tube. The samples are stored at −80° C.

Total amount of blood taken: less than 35 mL (chosen monkey weighs approximately 5 kg)

Anaesthesia: The monkey is intubated and controlled by respirator at a sevoflurane concentration of about 1.4-4%.

Infusion: Ringer-Acetate (Fresenius-Kabi) 0.5-1 ml/kg/h.

Monitoring

Body temperature, heart rate, ECG, $pCO_2$, $pO_2$, $SaO_2$ and blood pressure are monitored throughout the PET study.

Awakening 1 mL robinyl/neostigmin 2.5 mg is administered when the monkey shows signs of spontaneous breathing. Glucose 300 mg/ml is administered if necessary depending on the blood glucose state as measured.

$^{11}$C-PET-Studies

A bolus injection (i.v.) of approximately 5-20 MBq/kg of [$^{11}$C]Lu AE92686 is used in all studies. PET scanning and arterial blood sampling is commenced upon start of the administration of the radiolabelled compound.

PET: Emission Protocol

| | Frame Number | Accumulated time (minutes) |
|---|---|---|
| 12 frames à 10 seconds | 1-12 | 2 |
| 6 frames à 30 seconds | 13-18 | 5 |
| 5 frames à 2 minutes | 19-23 | 15 |
| 5 frames à 5 minutes | 24-28 | 40 |
| 5 frames à 10 minutes | 29-33 | 90 |

Total examination time: 90 minutes, 33 frames.

Reconstruction: filter Hann 4, 128 matrix.

Analysis of PET Data

Figure 1:
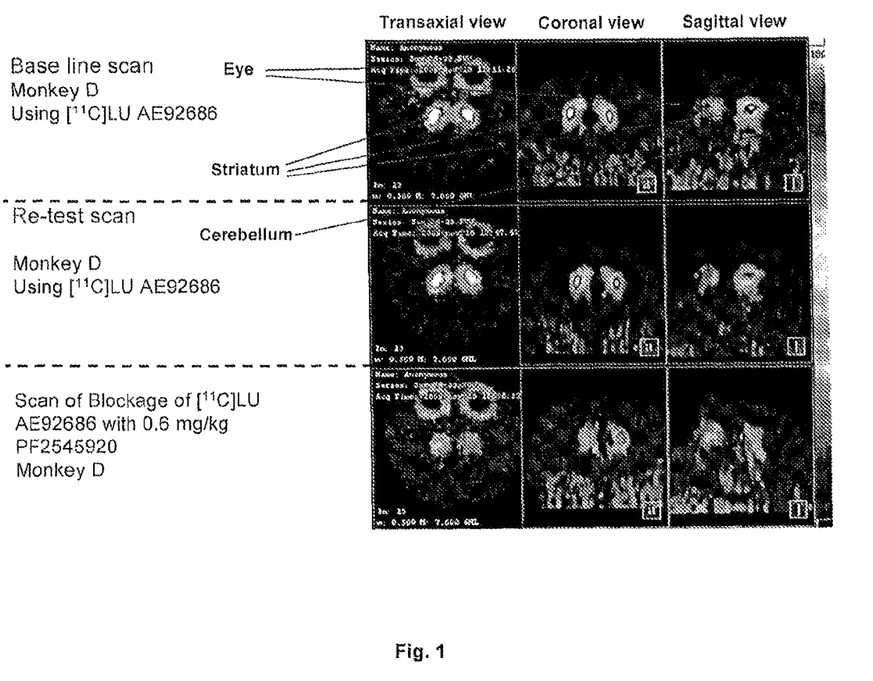
FIG. 1 shows PET SUV images, summation from 15 to 90 minutes after injection of [11C]Lu AE92686.

The results show, that [11C]Lu AE92686 readily enters the brain reaching peak regional tissue concentrations at approximately 10-15 minutes post injection followed by washout from brain regions known to be rich in PDE10A with highest uptake and retention observed in striaturn (FIG. 1 and FIG. 3): [11C]Lu AE92686 concentration was low in cerebellum (FIG. 1), a brain region known to possess very low level of PDE10A.

Example 5

Saturation of PDE10A Enzyme in the Brain

The selective PDE100A inhibitor PF2545920 (J. Med. Chem., 2009, 52 (16), pp 5188-5196) was administered intravenously, as an infusion over 15 minutes, starting 30 minutes prior to injection of the [11C]Lu AE92686 radiolabelled compound. PF2545920 was dissolved in 10% HPbetaCD in 0.9% NaCl, pH 4. Three blocking doses of PF2545920 were administered, at concentrations of the drug of 0.11 mg/kg (for the low dose), 0.6 mg/kg (for the middle dose) and 1.5 mg/kg (for the high dose).

Figure 2:
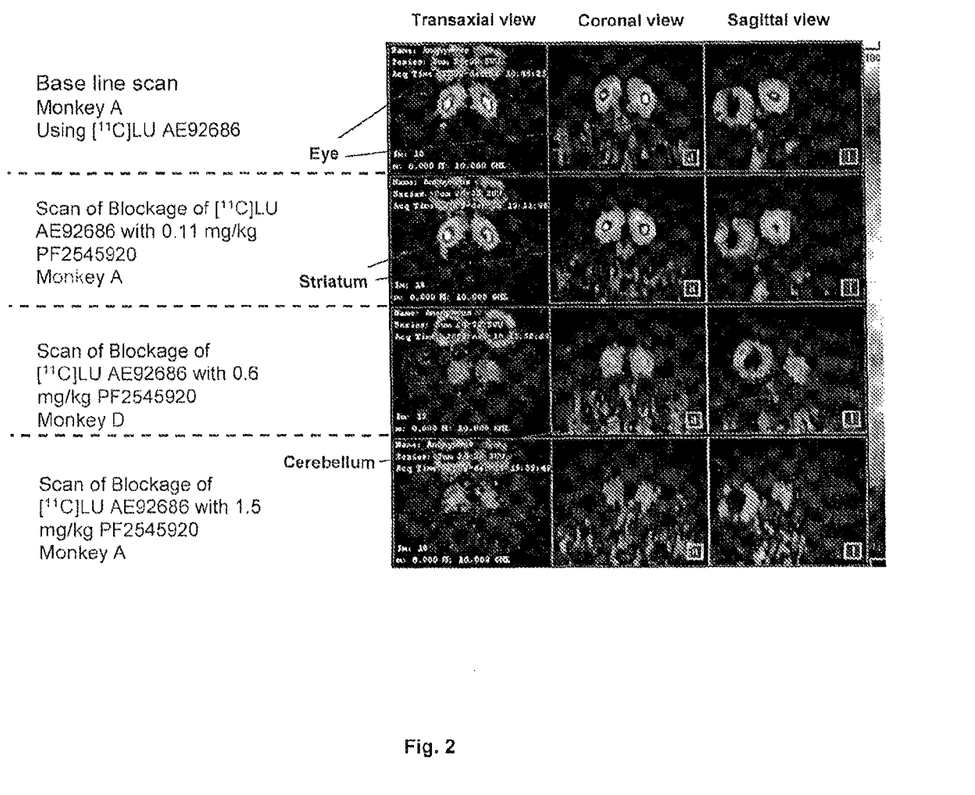
FIG. 2 shows PET SUV images, 15 to 90 minutes for two monkeys.
Figure 4:
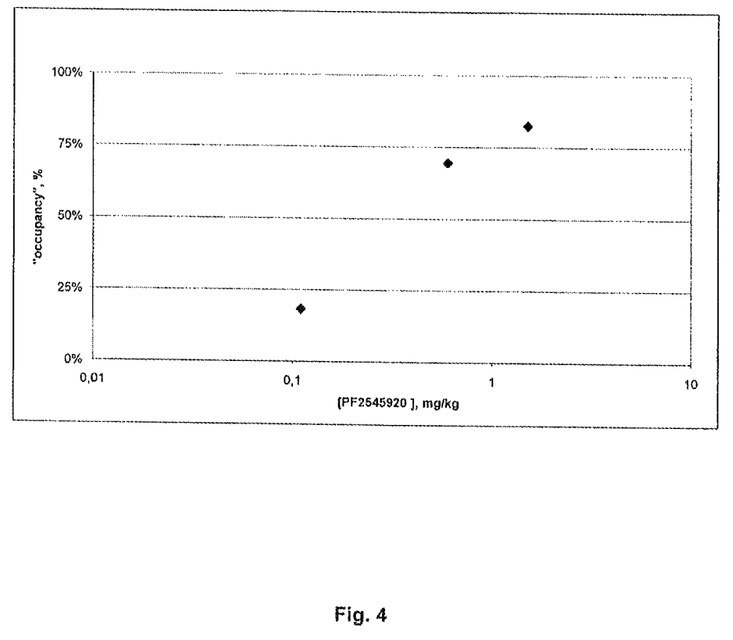
FIG. 4 shows a dose response curve picturing [11C]Lu AE92686 binding to striatum after challenge with three doses of the selective PDE10A inhibitor PF2545920.

The percent occupancy of PDE10A as a function of concentration of blocking substance was measured (FIG. 1 and FIG. 2) as well as the inter-individual variability of the brain kinetics of [11C]Lu AE92686 (FIG. 2). Cerebellum has been identified as the reference tissue due to its low content of PDE10A. Based on these measurements a dose-response curve was drawn (FIG. 4) showing the correlation between dose of PDE10 inhibitor PF2545920 and the occupancy of striatal PDE10A.

Figure 3:
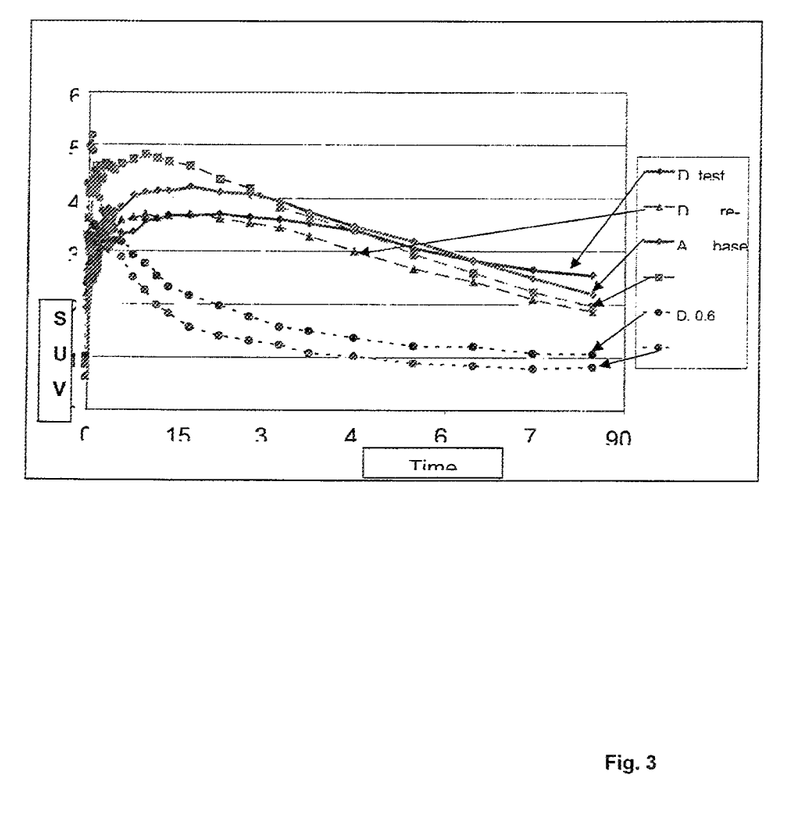
FIG. 3 shows kinetics of [11C]Lu AE92686 in striatum, results from two monkeys.

The Kinetics of the PET ligand [11C]Lu AE92686 in striatum was also measured at different doses in two different monkeys (FIG. 3)

The invention claimed is:
1. A compound according to Formula I comprising at least one isotope selected from the group consisting of $^{11}C$, $^{15}O$, and $^{18}F$, wherein
R1 is a radiolabelled group comprising at least one isotope selected from the group consisting of $^{11}C$, $^{15}O$, and $^{18}F$; and
R2-R7 are each individually selected from H, fluoro, methyl or methoxy;
or a salt or a hydrate form of the compound.

2. The compound of claim 1 wherein R3, R4, and R5 are H and R7 is $CH_3$.

3. The compound of claim 2 wherein R2 is H and R6 is $CH_3$.

4. The compound according to claim 3 wherein R1 is selected from the group consisting of
$^{11}CH_3$; $-CH_2{}^{11}CH_3$; $-^{11}CH_2CH_3$; $-CH_2CH_2{}^{11}CH_3$;
$-^{11}CH_2CH_2CH_3$; $-^{11}CH_2CH_2CH_2CH_3$;
$-CH_2CH_2CH_2{}^{11}CH_3$; $-CH_2CH_2{}^{18}F$;
$-CH_2CH_2CH_2CH_2{}^{18}F$.

5. The compound according to claim 4 wherein R1 is $^{11}CH_3$ [$^{11}C$]methyl).

6. The compound according to claim 1, wherein the compound is selected from the group consisting of
5,8-dimethyl-2-[2-([$^{11}C$-1-methyl]-4-phenyl-1H-imidazol-2-yl)-ethyl]-[1,2,4]triazolo[1,5-a]pyridine;
2-{2-[4-(2-[$^{11}C$]methoxy-phenyl)-1-methyl-1H-imidazol-2-yl]-ethyl}-5,8-dimethyl-[1,2,4]triazolo[1,5-a]pyridine; and
2-{2-[4-(2-[$^{18}F$]fluoro-phenyl)-1-methyl-1H-imidazol-2-yl]-ethyl}-5,8-dimethyl-[1,2,4]triazolo[1,5-a]pyridine.

7. A compound according to Formula I comprising at least one isotope selected from the group consisting of $^{11}C$, $^{15}O$, and $^{18}F$, wherein
when one or more of R2-R7 is a radiolabelled group comprising an isotope selected from the group consisting of $^{11}C$, $^{15}O$, and $^{18}F$; or
when one or more of R2-R5 is $^{18}F$;
then R1 is selected from the group consisting of H; $C_1$-$C_6$ alkyl; $C_1$-$C_6$alkyl($C_3$-$C_8$)cycloalkyl; $C_1$-$C_6$ hydroxyalkyl; fluoropropyl; fluoromethyl; and fluorobutyl;
or a salt or a hydrate form of the compound.

8. The compound of claim 7, wherein R3, R4, and R5 are H and R7 is $CH_3$.

9. The compound of claim 8 wherein R1 and R6 are $CH_3$.

10. The compound of claim 9 wherein R2 is $C^{11}CH_3$([$^{11}C$] methoxy).

11. The compound of claim 8 wherein R1 and R6 are $CH_3$.

12. The compound of claim 11 wherein R2 is $^{18}F$.

13. The compound of claim 2 wherein R1 is $CH_3$ and R2 is H.

14. The compound of claim 13 wherein R6 is $O^{11}CH_3$ ([$^{11}C$]methoxy).

15. The compound of claim 7 wherein R1 is methyl, ethyl, 1-propyl, 2-propyl, or isobutyl.

16. The compound of claim 7 wherein R1 is cyclopropylmethyl or hydroxyethyl.

17. The compound of claim 6, wherein the compound is 5,8-dimethyl-2-[2-([$^{11}C$-1-methyl]-4-phenyl-1H-imidazol-2-yl)-ethyl]-[1,2,4]triazolo[1,5-a]pyridine.

* * * * *

UNITED STATES PATENT AND TRADEMARK OFFICE
CERTIFICATE OF CORRECTION

PATENT NO. : 8,592,449 B1
APPLICATION NO. : 13/890705
DATED : November 26, 2013
INVENTOR(S) : Jan Kehler et al.

It is certified that error appears in the above-identified patent and that said Letters Patent is hereby corrected as shown below:

In the Claims:

In Claim 4, at column 15, line 34, please insert -- -$CH_2CH_2CH_2{}^{18}F$; -- after "-$CH_2CH_2{}^{18}F$;".

Signed and Sealed this
Sixth Day of May, 2014

Michelle K. Lee
*Deputy Director of the United States Patent and Trademark Office*